United States Patent [19]

Besancon et al.

[11] Patent Number: 4,661,338
[45] Date of Patent: Apr. 28, 1987

[54] PROCESS FOR DETERMINING HYPOACIDITY

[75] Inventors: François Besancon; François Chast, both of Paris, France

[73] Assignee: Societe d'Etudes Scientifiques et Industrielles de l'Ile de France, Paris, France

[21] Appl. No.: 442,965

[22] Filed: Nov. 19, 1982

[30] Foreign Application Priority Data

Nov. 20, 1981 [FR] France ............................. 81 21739

[51] Int. Cl.⁴ .............................................. A61K 49/00
[52] U.S. Cl. .......................................... 424/7.1; 424/9
[58] Field of Search .............. 436/163, 101, 100, 166, 436/169; 422/57; 424/7.1, 9

[56] References Cited

U.S. PATENT DOCUMENTS

| | | | |
|---|---|---|---|
| 3,447,904 | 6/1969 | Rupe | 422/57 |
| 3,904,373 | 9/1975 | Haper | 422/57 |
| 4,056,609 | 11/1977 | Kirchubel . | |
| 4,200,110 | 4/1980 | Peterson et al. . | |

FOREIGN PATENT DOCUMENTS 1082750 8/1966 United Kingdom .

OTHER PUBLICATIONS

"Studies on Gastritis in the Upper Portion of Stomach by Endoscopic Congo Red Test," by M. Tatsuta et al., Endoscopy, vol. 5, pp. 61-69 (1973).

*Primary Examiner*—Sam Rosen
*Attorney, Agent, or Firm*—Fitzpatrick, Cella, Harper & Scinto

[57] ABSTRACT

A method is provided for rapidly screening candidates for precancerous atrophic H. gastritis by visualizing the presence of a hypoacidity condition of the gastric mucous membrane by applying droplets of an indicator to the stomach wall which indicator undergoes a marked color change in the presence of a hypoacidic condition and then detecting immediately the presence of that color change. The indicator employed is bromocresol green, bromophenol blue or bromochlorophenol blue.

3 Claims, No Drawings

PROCESS FOR DETERMINING HYPOACIDITY

The present invention concerns a novel process for determining hypoacidity of the gastric mucous membrane in the course of gastroscopy and a colored indicator for carrying the process into effect.

The full importance of determining hypoacidity during gastroscopy will be better appreciated when it is understood that such hypoacidity is a sign of atrophic H gastritis. Atrophic H gastritis is a condition which fosters a predisposition to cancer. It is therefore essential to be able to identify patients for whom observation is indicated. In addition, determining such hypoacidity makes it possible either to designate areas which require biopsy, or to avoid carrying out such a biopsy when it is not necessary.

Various processes have been used hitherto for determining the degree of acidity of the gastric mucous membrane.

A process of measuring the pH-value has been used. In that process, a glass micro-electrode attached to a fibroscope or passed into the fibroscope, gave access to the gastric mucous membrane and made it possible to determine the pH-value thereof. That process is not being used at the present time, as the equipment required is very fragile, expensive and difficult to use, and the data obtained is questionable.

Another process proposed involves using a coloring agent, namely CONGO red, for determining the degree of acidity of the gastric mucous membrane. The procedure employed in that method is described in an article by S. OKUDA, T. SAEGUSA, H. INUI and N. SENDA entitled 'An endoscopic method to investigate the gastric acid secretion' which was published after the First Congress of the International Endoscopy Society which took place in Tokyo in 1966.

The procedure is as follows and employs the steps of:

1. Pre-treatment by administering atropine and butyl-scopolamine bromide.
2. Subcutaneous injection of 30 mg of antihistamine (of diphenhydramine hydrochloride type), 15 to 30 minutes before administration of stimulants described hereinafter.
3. Washing out the stomach with a 5 percent sodium bicarbonate solution.
4. Administration of the coloring agent: 20 to 30 ml of 0.3 percent Congo red are passed into the stomach by means of a catheter and applied to the gastric wall causing the patient to change position, or by massaging the patient's abdomen.
5. Subcutaneous injection of stimulants for secretion of gastric acidity.
6. Endoscopic observations by means of a fibroscope, which observations are to take place between 20 and 30 minutes after the injection of stimulants, the delay period being necessary due to the time for response of the coloring agent to the secretion of gastric acid. The coloring agent changes to blue-black in color only when pH-value is reduced from 5 to 2.8.

Another procedure which is very close to that described above is described in the review Endoscopy 5 (1973), 61-69.

In both cases, it is important to carefully follow the lengthy and difficult constraints to which the patient must be subjected, before and during the endoscopy operation.

The present invention therefore concerns a process for determining the degree of acidity of the gastric mucous membrane by means of a coloring agent. The present process is distinguished from the state of the art in that it avoids the preliminary washing out of the stomach and the stimulation of gastric secretion.

The process according to the invention also has the advantage of giving an immediate reading. There is no need to subject a patient to a useless and frustrating delay period while awaiting a pH change. It therefore avoids any increase in the length of a distressing test.

More specifically, the process according to the invention comprises determining hypoacidity of the gastric mucous membrane by using a coloring agent. The change in color of the agent permits an immediate fibroscopic reading as soon as the agent comes into contact with a hypoacidic region of the gastric mucous membrane generally at a pH greater than about 3.

There are many existing pH sensitive coloring agents. It has been found that only certain coloring agents meet the various criteria which are required. Important factors to be met are toxicity, since the coloring agent is introduced directly into the patient's stomach, and color, since the indicator should stand out clearly against the mucous membrane when it is hypoacid.

Of the coloring agents which satisfy these criteria and which are compatible with the process of this invention, bromocresol green of the following formula is preferred:

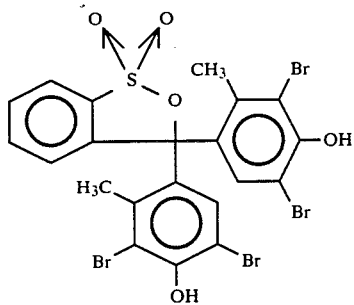

Bromocresol green has the advantage of possessing zero acute toxicity, when administered orally in a male mouse at doses of 300 mg/kg, in a 1 percent solution. In addition, this coloring agent immediately changes color to blue-green when the pH-value rises from 3.5 to 5, which color can be easily detected on the hypoacid gastric mucous membrane.

In practice, the coloring agents of the invention, including bromocresol green, are used in solution in a proportion of 1/1000 to ethanol and water. Usually it is only necessary to deposit a few drops of that solution on the mucous membrane by means of a catheter which is passed into the gastro-fibroscope in order to observe any hypo-acidity in the stomach and in particular, in the fundus. The solution may contain glycerine or any other substance which promotes immobilization of the deposited reactant in place.

By virtue of the coloring agent of the invention the endoscopy operation is neither complicated nor prolonged, and there is no need to specially prepare the stomach of the patient, as required when using Congo red. Congo red is also less favorable, since it is red in a hypoacid medium and therefore cannot be readily detected on the wall of the stomach. Its blue-black color occurs only when the pH-value is less than 3, that is to say, in a strongly acid medium and not a hypoacidic medium.

Other colored indicators which can also be used in this invention are bromophenol blue (yellow at a pH-value of 3 and violet at a pH-value of 4.6) and bromochlorophenol blue (yellow at pH-value of 3 and blue at pH-value of 4.6). Such indicators are less preferable than the preferred bromocresol green, since they change color at a lower pH-value than bromocresol green. The invention is not to be limited except as set forth in the following claims:

What is claimed is:

1. A method for rapidly screening candidates by visualizing the presence of a hypoacidity condition of the gastric mucous membrane which comprises: (a) applying to a stomach wall droplets of an indicator selected from the group consisting of bromocresol green, bromophenol blue or bromochlorophenol blue, which indicator undergoes a marked color change in the presence of a hypoacidic condition; and (b) detecting immediately the presence or absence of said color change on the stomach wall to which said droplets are applied in order to promptly screen the candidates for hypoacidity of the gastric mucous membrane.

2. The process of claim 1 wherein the indicator is bromocresol green in a 1/1000 hydro-alcoholic solution.

3. The process according to claim 2 in which the hydro-alcoholic solution further comprises glycerine.

* * * * *